(12) United States Patent
Sisler

(10) Patent No.: US 6,194,350 B1
(45) Date of Patent: Feb. 27, 2001

(54) METHODS OF BLOCKING ETHYLENE RESPONSE IN PLANTS USING CYCLOPROPENE DERIVATIVES

(75) Inventor: Edward C. Sisler, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/448,523

(22) Filed: Nov. 23, 1999

(51) Int. Cl.$^7$ .......................... A01N 27/00; A01N 29/02
(52) U.S. Cl. ............................. 504/114; 504/357
(58) Field of Search ..................... 504/114, 357

(56) References Cited

U.S. PATENT DOCUMENTS

| | | | |
|---|---|---|---|
| 3,879,188 | 4/1975 | Fritz et al. | 71/86 |
| 5,100,462 | 3/1992 | Sisler et al. | 71/121 |
| 5,518,988 | 5/1996 | Sisler et al. | 504/114 |
| 6,017,849 | * 1/2000 | Daly et al. | 504/114 |

OTHER PUBLICATIONS

M.C. Pirrung, *Proposal to the Fred C. Gioeckner Foundation* (1991).
Pirrung et al. "Ethylene Biosynthesis, Aminocyclopropene Carboxylic Acid", J. Chem Soc., Chem. Commun., (13), 857–859 (1989).
Wheeler et al., "Synthesis of 1–Aminocyclopropene Carboxylic Acid", J. Org. Chem., 52(22) 4875–4877 (1987).
ACS Registry, Registration Number 3569–41–3 (1999).
ACS Registry, Registration Number 50915–82–7 (1999).
ACS Registry, Registration Number 50915–83–8 (1999).
ACS Registry, Registration Number 503–05–09 (1999).
ACS Registry, Registration Number 5026–66–4 (1999).
ACS Registry, Registration Number 18325–59–2 (1999).
ACS Registry, Registration Number 18459–83–1 (1999).
ACS Registry, Registration Number 28634–53–9 (1999).
ACS Registry, Registration Number 50915–84–9 (1999).
ACS Registry, Registration Number 79246–40–5 (1999).
ACS Registry, Registration Number 223105–97–3 (1999).
ACS Registry, Registration Number 35365–52–7 (1999).
ACS Registry, Registration Number 35365–53–8 (1999).
ACS Registry, Registration Number 1089–40–3 (1999).
ACS Registry, Registration Number 178493–45–3 (1999).
ACS Registry, Registration Number 24471–15–6 (1999).
ACS Registry, Registration Number 141493–84–7 (1999).
ACS Registry, Registration Number 152389–89–4 (1999).
ACS Registry, Registration Number 24471–16–7 (1999).
ACS Registry, Registration Number 152389–90–7 (1999).
ACS Registry, Registration Number 3565–59–1 (1999).
ACS Registry, Registration Number 183888–89–7 (1999).
ACS Registry, Registration Number 102179–95–3 (1999).
ACS Registry, Registration Number 183888–58–6 (1999).
ACS Registry, Registration Number 738–87–4 (1999).
ACS Registry, Registration Number 39647–67–1 (1999).
ACS Registry, Registration Number 39647–66–0 (1999).
ACS Registry, Registration Number 3220–60–8 (1999).
ACS Registry, Registration Number 39647–65–9 (1999).
ACS Registry, Registration Number 152442–29–0 (1999).
ACS Registry, Registration Number 13487–77–9 (1999).
ACS Registry, Registration Number 183888–62–2 (1999).
ACS Registry, Registration Number 183888–63–3 (1999).
ACS Registry, Registration Number 183888–65–5 (1999).
ACS Registry, Registration Number 109154–74–7 (1999).
ACS Registry, Registration Number 102127–48–0 (1999).

* cited by examiner

*Primary Examiner*—S. Mark Clardy
(74) *Attorney, Agent, or Firm*—Myers Bigel Sibley & Sajovec

(57) ABSTRACT

Methods of applying $C_{6-20}$ alkyl cyclopropene derivatives and compositions thereof to block ethylene receptors in plants are disclosed. One such method comprises applying to the plant an effective ethylene response-inhibiting amount of cyclopropene derivatives or compositions thereof. Also disclosed are methods of inhibiting abscission in plants and methods of prolonging the life of cut flowers.

69 Claims, No Drawings

METHODS OF BLOCKING ETHYLENE RESPONSE IN PLANTS USING CYCLOPROPENE DERIVATIVES

This invention was made with government support under Grant No. US-2786-96R awarded by the U.S. Department of Agriculture. The government has certain rights in the invention.

FIELD OF THE INVENTION

The present invention generally relates to methods of blocking ethylene responses in plants and plant materials, and particularly relates to methods of inhibiting various ethylene responses including plant maturation and degradation by applying cyclopropene derivatives and compositions thereof to plants.

BACKGROUND OF THE INVENTION

Ethylene is known to mediate a variety of growth phenomena in plants. See generally Fritz et al. U.S. Pat. No. 3,879,188. This activity is understood to be achieved through a specific ethylene receptor in plants. Many compounds other than ethylene interact with this receptor: some mimic the action of ethylene; others prevent ethylene from binding and thereby counteract its action.

Many compounds that block the action of ethylene do so by binding to the ethylene binding site. Unfortunately, they often diffuse from the binding site over a period of several hours. See E. Sisler and C. Wood, Plant Growth Reg. 7, 181–191 (1988). These compounds may be used to counteract ethylene action. A problem with such compounds, however, is that exposure must be continuous if the effect is to last for more than a few hours.

Photoaffinity labeling has been used in biological studies to label binding sites in a permanent manner: usually by generating a carbene or nitrene intermediate. Such intermediates are very reactive and react rapidly and indiscriminately with many things. A compound already bound, however, would react mostly with the binding site. In a preliminary study, it was shown that cyclopentadiene was an effective blocking agent for ethylene binding. See E. Sisler et al., Plant Growth Reg. 9, 157–164 (1990). Methods of combating the ethylene response in plants with diazocyclopentadiene and derivatives thereof are disclosed in U.S. Pat. No. 5,100,462 to Sisler et al. U.S. Pat. No. 5,518,988 to Sisler et al. describes the use of cyclopropenes having a $C_1$ to $C_4$ alkyl group to block the action of ethylene.

Notwithstanding these efforts, there remains a need in the art for improved plant maturation and degradation regulation.

SUMMARY OF THE INVENTION

Methods of inhibiting an ethylene response in a plant are disclosed herein. According to the present invention, one such method comprises applying to the plant an effective ethylene response-inhibiting amount of a cyclopropene derivative or a composition thereof described further in detail herein. Long-chain cyclopropene derivatives are particularly preferred as described below.

Another aspect of the present invention is a method of blocking ethylene receptors in plants by applying to the plants an effective ethylene receptor-blocking amount of a cyclopropene derivative or a composition thereof.

Also disclosed is a method of inhibiting abscission in a plant, comprising applying to the plant an effective abscission-inhibiting amount of a cyclopropene derivative or a composition thereof.

Also disclosed is a method of prolonging the life of a cut flower, comprising applying to the cut flower an effective life-prolonging amount of a cyclopropene rivative or a composition thereof.

The methods described herein may be carried out in a number of suitable manner, such as by contacting the plant with a cyclopropene derivative or a composition thereof, whether in solid, liquid, or gaseous form, or by introducing the plant or cut flower into an atmosphere infused with the cyclopropene derivative or a composition thereof. These and other suitable methods of application are discussed in detail below.

Also disclosed is the use of a cyclopropene derivative as described herein for the preparation of an agricultural composition for carrying out any of the methods described above.

DETAILED DESCRIPTION OF THE INVENTION

Cyclopropene derivatives which may be used to carry out the present invention are defined by Formula I:

(I)

wherein:

n is a number from 1 to 4. Preferably n is 1 or 2, and most preferably n is 1.

R is a saturated or unsaturated, linear or branched-chain, unsubstituted or substituted, $C_6$ to $C_{20}$ alkyl, alkenyl, or alkynyl.

The terms "alkyl", "alkenyl", and "alkynyl", as used herein, refer to linear or branched alkyl, alkenyl or alkynyl substituents. The terms should be interpreted broadly and may include compounds in which one or more of the carbons in the chain is replaced by heteroatoms such as oxygen or nitrogen, ester groups, nitrites and their salts, acids and their salts and esters, or where such chains include halogen, amino, alkoxy, carboxy, alkoxycarbonyl, or hydroxy substituents. Examples include, but are not limited to, hexyl, heptyl, octyl, nonyl, and decyl. Alkyl groups of the present invention are preferably linear and saturated.

Cyclopropene derivatives which may be used to carry out the present invention may be prepared by various methods known to those skilled in the art. For example, 1-substituted cyclopropenes can be prepared from 1,1,3-tribromo substituted cyclopropanes as described by Baird et al. in *Preparation and Lithiation of 1-Halogenocyclopropenes*, J. CHEM. SOC. PERKIN TRANS. I 1845–53 (1986). Additionally, 3,3-Substituted clyclopropenes can be prepared using methods described by N. I. Yakushkina and I. G. Bolesov in *Dehydrohalogenation of Monohalogenocyclopropanes as a Method for the Synthesis of Sterically Screened Cyclopropenes*, RUSSIAN J. OF ORGANIC CHEM. 15:853–59 (1979).

Agricultural compositions comprising the compounds defined by Formula (I) described above are also encompassed by the invention. Preferably the compositions comprise between 0.005 to 99% by weight of the active compounds of the present invention may be formed. These compositions may optionally include various additives typically found in agricultural compositions including, but not limited to, carriers, adjuvants, wetting agents and the like.

Numerous organic solvents may be used as carriers for the active compounds of the present invention, e.g., hydrocarbons such as hexane, benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as solutions or emulsions, can also be employed as inert carriers for the active compounds.

The active compounds of the present invention may also include adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, tripoli, wood flour, walnut shell flour, redwood flour and lignin.

It may be desirable to incorporate a wetting agent in the compositions of the present invention. Such wetting agents may be employed in both the solid and liquid compositions. The wetting agent can be anionic, cationic or nonionic in character.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium stearate and potassium oleate, sodium salt of the sulfonated monoglyceride of coconut fatty acids, sorbitan, sesquioleate, lauryl trimethyl ammonium chloride, octadecyl trimethyl ammonium chloride, polyethylene glycol lauryl ether, polyethylene esters of fatty acids and rosin acids (e.g., Ethofat® 7 and 13, commercially available from Akzo Nobel Chemicals, Inc. of Chicago, Ill.), sodium N-methyl-N-oleyltaurate, Turkey Red oil, sodium dibutylnaphthalene sulfonate, sodium lignin sulfonate (Maraspersee®N, commercially available from LignoTech USA of Rothschild, Wisc.), polyethylene glycol stearate, sodium dodecylbenzene sulfonate, tertiary dodecyl polyethylene glycol thioether, long chain ethylene oxide-propylene oxide condensation products (e.g., Pluronic® 61 (molecular weight 1,000) commercially available from BASF of Mount Olive, N.J.), sorbitan sesquioleate, polyethylene glycol ester of tall oil acids, sodium octyl phenoxyethoxyethyl sulfate, polyoxyethylene (20) sorbitan monolaurate (Tween® 20, commercially available from ICI Americas Inc. of Wilmington, Del.) tris (polyoxyethylene) sorbitan monostearate (Tween® 60, commercially available from ICI Americas Inc. of Wilmington, Del.), and sodium dihexyl sulfosuccinate.

The solid, liquid, and gaseous formulations can be prepared by various conventional procedures. Thus, the active ingredient, in finely divided form if a solid, may be tumbled together with finely divided solid carrier. Alternatively, the active ingredient in liquid form, including mixtures, solutions, dispersions, emulsions and suspensions thereof, may be admixed with the solid carrier in finely divided form. Furthermore, the active ingredient in solid form may be admixed with a liquid carrier to form a mixture, solution, dispersion, emulsion, suspension or the like.

The active compounds of the present invention can be applied to plants by various suitable means. For example, an active compound may be applied alone in gaseous, liquid, or solid form by contacting the compound with the plant to be treated. Additionally the active compound may be converted to the salt form, and then applied to the plants. Alternatively, compositions containing one or more active compounds of the present invention may be formed. The compositions may be applied in gaseous, liquid, or solid form by contacting the composition with the plant to be treated. Such compositions may include an inert carrier. Suitable solid carriers include dusts. Similarly, when in gaseous form, the compound may be dispersed in an inert gaseous carrier to provide a gaseous solution. The active compound may also be suspended in a liquid solution such as an organic solvent or an aqueous solution that may serve as the inert carrier. Solutions containing the active compound may be heterogeneous or homogeneous and may be of various forms including mixtures, dispersions, emulsions, suspensions and the like.

The active compounds and compositions thereof can also be applied as aerosols, e.g., by dispersing them in air using a compressed gas such as dichlorodifluoromethane, trichlorofluoromethane, and other Freons, for example.

The term "plant" is used in a generic sense herein, and includes woody-stemmed plants such as trees and shrubs. Plants to be treated by the methods described herein include whole plants and any portions thereof, such as field crops, potted plants, cut flowers (stems and flowers), and harvested fruits and vegetables.

Plants treated with the compounds and by the methods of the present invention are preferably treated with a non-phytotoxic amount of the active compound.

The present invention can be employed to modify a variety of different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the prolongation of the life of ornamentals such as potted plants, cut flowers, shrubbery, and dormant seedlings, in some plants (e.g., pea) the inhibition of growth, and in other plants (e.g., rice) the stimulation of growth. Additional ethylene responses or ethylene-type responses that may be inhibited by active compounds of the present invention include, but are not limited to, auxin activity, inhibition of terminal growth, control of apical dominance, increase in branching, increase in tillering, changing biochemical compositions of plants (such as increasing leaf area relative to stem area), abortion or inhibition of flowering and seed development, lodging effects, stimulation of seed germination and breaking of dormancy, and hormone or epinasty effects.

Vegetables which may be treated by the method of the present invention to inhibit ripening and/or senescence include leafy green vegetables such as lettuce (e.g., *Lactuea sativa*), spinach (*Spinaca oleracea*), and cabbage (*Brassica oleracea*), various roots, such as potatoes (*Solanum tuberosum*) and carrots (Daucus), bulbs, such as onions (Allium sp.), herbs, such as basil (*Ocimum basilicum*), oregano (*Origanum vulgare*), dill (*Anethum graveolens*), as well as soybean (*Glycine max*), lima beans (*Phaseolus limensis*), peas (Lathyrus spp.), corn (*Zea mays*), broccoli (*Brassica oleracea italica*), cauliflower (*Brassica oleracea botrytis*), and asparagus (*Asparagus officinalis*).

Fruits which may be treated by the method of the present invention to inhibit ripening include tomatoes (*Lycopersicon esculentum*), apples (*Malus domestics*), bananas (*Musa sapientum*), pears (*Pyrus communis*), papaya (*Carica papaya*), mangoes (*Mangifera indica*), peaches (*Prunus persica*), apricots (*Prunus armeniaca*), nectarines (*Prunus persica nectarina*), oranges (*Citrus sp.*), lemons (*Citrus limonia*), limes (*Citrus aurantifolia*), grapefruit (*Citrus paradisi*), tangerines (*Citrus nobils deliciosa*), kiwi (*Actinidia chinenus*), melons such as cantaloupe (*C. cantalupensis*) and musk melon (*C. melo*), pineapple (*Aranas comosus*), persimmon (*Diospyros sp.*), various small fruits including berries such as strawberries (Fragaria), blueberries (*Vaccinium sp.*) and raspberries (e.g., *Rubus ursinus*), green beans (*Phaseolus vulgaris*), members of the genus Cucumis such as cucumber (*C. sativus*), and avocados (*Persea americana*).

Ornamental plants which may be treated by the method of the present invention to inhibit senescence and/or to prolong flower life and appearance (e.g., delay wilting), include potted ornamentals, and cut flowers. Potted ornamentals and cut flowers which may be treated with the present invention include azalea (Rhododendron spp.), hydrangea (*Macrophylla hydrangea*), hybiscus (*Hibiscus rosasanensis*), snapdragons (Antirrhinum sp.), poinsettia (*Euphorbia pulcherima*), cactus (e.g. *Cactaceae schlumbergera truncata*), begonias (Begonia sp.), roses (Rosa spp.), tulips (Tulipa sp.), daffodils (Narcissus spp.), petunias (*Petunia hybrida*), carnation (*Dianthus caryophyllus*), lily (e.g., Lilium sp.), gladiolus (Gladiolus sp.), alstroemeria (*Alstoemeria brasiliensis*), anemone (e.g., *Anemone blanda*), columbine (Aquilegia sp.), aralia (e.g., *Aralia chinensis*), aster (e.g., *Aster carolinianus*), bougainvillea (Bougainvillea sp.), camellia (Camellia sp.), bellflower (Campanula sp.), cockscomb (celosia sp.), falsecypress (Chamaecyparis sp.), chrysanthemum (Chiysanthemum sp.), clematis (Clematis sp.), cyclamen (Cyclamen sp.), freesia (e.g., *Freesia refracta*), and orchids of the family Orchidaceae.

Plants which may be treated by the method of the present invention to inhibit abscission of foliage, flowers and fruit include cotton (Gossypium spp.), apples, pears, cherries (*Prunus avium*), pecans (*Carva illinoensis*), grapes (*Vitis vinifera*), olives (e.g. *Vitis vinifera* and *Olea europaea*), coffee (*Coffea arabica*), snapbeans (*Phaseolus vulgaris*), and weeping fig (*ficus benjamina*), as well as dormant seedlings such as various fruit trees including apple, ornamental plants, shrubbery, and tree seedlings. In addition, shrubbery which may be treated according to the present invention to inhibit abscission of foliage include privet (Ligustrum sp.), photinea (Photinia sp.), holly (Ilex sp.), ferns of the family Polypodiaceae, schefflera (Schefflera sp.), aglaonema (Aglaonema sp.), cotoneaster (Cotoneaster sp.), barberry (Berberis sp.), waxmyrtle (Myrica sp.), abelia (Abelia sp.), acacia (Acacia sp.) and bromeliades of the family Bromeliaceae.

Active compounds of the present invention have proven to be unexpectedly potent inhibitors of ethylene action on plants, fruits and vegetables, even when applied at low concentrations. Among other things, compounds of the present invention may result in a longer period of insensitivity to ethylene than compounds found in the prior art. This longer period of insensitivity may occur even when compounds of the present invention are applied at a lower concentration than previous compounds.

The present invention is explained in greater detail in the following non-limiting Examples. In these examples, μl means microliters; ml means milliliters; nl means nanoliters; l means liters; cm means centimeters; and temperatures are given in degrees Celcius.

COMPARATIVE EXAMPLE A

Activity of Short-Chain Cyclopropene Derivatives

To obtain the minimum concentration that protected bananas from 333 μl/l of ethylene, compounds described in U.S. Pat. No. 5,518,988 to Sisler et al. were applied to bananas according to the methods setforth herein. A known amount of an active compound was injected as a gas into a 3-liter jar containing a banana. The jar was sealed and the banana was removed after 24 hours. At the end of exposure, the banana was treated with 333 μl/l of ethylene in a 3-liter jar for 12–15 hours. It was then observed for ripening. The minimum concentration is the minimum concentration that protected the banana from 333 μl/l of ethylene. Ten microliters/liter of ethylene is usually considered to be a saturating amount.

To obtain the time of protection, bananas were exposed to a saturating amount of the compound for 24 hours (this was done as above and at least 10 times the minimum protection amount was used). After exposure, bananas were removed from the jars and each day individual bananas were exposed to 333 μl/l of ethylene for 12–15 hours. The day the bananas responded to ethylene was recorded as the protection time. The results are shown in Table A.

TABLE A

Minimum Concentration and Time of Insensitivity for 1-Cyclopropenes Described in U.S. Pat. No. 5,518,988 to Sisler et al.

| Compound | Structure | Concentration (nl/l) | Time (days) |
| --- | --- | --- | --- |
| cyclopropene (CP) | △ | 0.7 | 12 |
| 1-methylcyclopropene (1-MCP) | △—CH$_3$ | 0.7 | 12 |
| 1-ethylcyclopropene (1-ECP) | △—CH$_2$CH$_3$ | 4 | 12 |
| 1-propylcyclopropene (1-PCP) | △—CH$_2$CH$_2$CH$_3$ | 6 | 12 |
| 1-butylcyclopropene (1-BCP) | △—CH$_2$(CH$_2$)$_2$CH$_3$ | 3 | 12 |

EXAMPLE 1

Compounds of the Present Invention: Minimum Concentration for Protection

To obtain the minimum concentration that protected bananas from 333 μl/l of ethylene, compounds according to the present invention were applied to bananas according to the method described herein. A known amount of the active compound was placed on filter paper in a 3-liter jar to facilitate evaporation into the vapor state. The compounds were applied in an ethyl ether solution because the amount used was potentially too small to apply unless they were in solution. The amount of ether (about 10 μl in 3 l) was without effect when applied alone on a banana contained in a 3-liter jar. The jar was sealed and the banana was removed after 4 hours of exposure. At the end of exposure, the banana was treated with 333 μl/l of ethylene in a 3-liter jar for 12–15 hours. It was then observed for ripening. The minimum concentration is the concentration that protected the bananas from 333 μl/l of ethylene. Ten microliters/liter of ethylene is usually considered to be a saturating amount. This procedure was repeated for 8-, 24- and 48-hour treatment times to determine the minimum concentration of active compounds of the present invention needed to provide protection from 333 μl/l of ethylene for a given treatment time. The results are shown in Table 1.

TABLE 1

Treatment Time and Minimum Concentration of 1-Cyclopropenes of the Present Invention on Banana Fruit

| Active Compound | Treatment Time (hours) | Minimum Concentration (nl/l) |
|---|---|---|
| 1-hexylcyclopropene | 4 | 12.0 |
|  | 8 | 0.8 |
|  | 24 | 0.4 |
|  | 48 | 0.3 |
| 1-octylcyclopropene | 4 | 0.8 |
|  | 8 | 0.45 |
|  | 24 | 0.3 |
|  | 48 | 0.25 |

EXAMPLE 2

Compounds of the Present Invention: Time of Protection

To obtain the time of protection, bananas were exposed to a saturating amount of the compound for 24 hours (this was done as described in Example 1 above and at least 10 times the minimum protection amount was used). After exposure, bananas were removed from the jars and each day individual bananas were exposed to 333 μl/l of ethylene for 12–15 hours. The day the bananas responded to ethylene was recorded as the protection time. The results are shown in Table 2.

TABLE 2

Minimum Concentration and Time of Insensitivity for 1-Cyclopropenes Provided by the Present Invention

| Active Compound | Structure | Concentration (nl/l) | Time (days) |
|---|---|---|---|
| 1-hexylcyclopropene (1-HCP) | △—CH₂(CH₂)₄CH₃ | 0.4 | 20 |
| 1-octylcyclopropene (1-OCP) | △—CH₂(CH₂)₆CH₃ | 0.3 | 25 |

The foregoing embodiments and examples are illustrative of the present invention and are not to be construed as limiting thereof. The invention is defined by the following claims, with equivalents of the claims to be included therein.

That which is claimed is:

1. A method of inhibiting an ethylene response in a plant, comprising applying to the plant an effective ethylene response-inhibiting amount of a compound of Formula I:

(I)

wherein:
n is a number from 1 to 4; and
each R is independently a saturated or unsaturated, linear or branched-chain, unsubstituted or substituted, $C_6$ to $C_{20}$ alkyl, alkenyl, or alkynyl.

2. A method according to claim 1, wherein n is 1 or 2.
3. A method according to claim 1, wherein n is 1.
4. A method according to claim 1, wherein said applying step is carried out by contacting said plant to a gas of said compound.
5. A method according to claim 1, wherein said applying step is carried out by spraying said plant with a solution comprising said compound.
6. A method according to claim 1, wherein said applying step is carried out by contacting said plant to a solid comprising said compound.
7. A method according to claim 1, wherein said ethylene response is fruit ripening.
8. A method according to claim 1, wherein said ethylene response is vegetable ripening.
9. A method according to claim 1, wherein said ethylene response is flower senescence.
10. A method according to claim 1, wherein at least one R is an alkyl, alkenyl, or alkynyl substituted with at least one substituent selected from the group consisting of halogen, amino, alkoxy, carboxy, alkoxycarbonyl, and hydroxy.
11. A method according to claim 1, wherein at least one of the carbon atoms in at least one R group is replaced by at least one constituent selected from the group consisting of ester groups, nitriles, amines, amine salts, acids, acid salts, esters of acids, hydroxyl groups, and heteroatoms selected from the group consisting of oxygen and nitrogen.
12. A method according to claim 3, wherein R is hexyl.
13. A method according to claim 3, wherein R is octyl.
14. A method of inhibiting abscission in a plant, comprising applying to the plant an effective abscission-inhibiting amount of a compound of Formula I:

(I)

wherein:
n is a number from 1 to 4; and
each R is independently a saturated or unsaturated, linear or branched-chain, unsubstituted or substituted, $C_8$ to $C_{20}$ alkyl, alkenyl, or alkynyl.

15. A method according to claim 14, wherein n is 1 or 2.
16. A method according to claim 14, wherein n is 1.
17. A method according to claim 14, wherein said applying step is carried out by contacting said plant to a gas of said compound.
18. A method according to claim 14, wherein said applying step is carried out by spraying said plant with a solution comprising said compound.
19. A method according to claim 14, wherein said applying step is carried out by contacting said plant to a solid comprising said compound.

20. A method according to claim 14, wherein at least one R is an alkyl, alkenyl, or alkynyl substituted with at least one substituent selected from the group consisting of halogen, amino, alkoxy, carboxy, alkoxycarbonyl, and hydroxy.

21. A method according to claim 14, wherein at least one of the carbon atoms in at least one R group is replaced by at least one constituent selected from the group consisting of ester groups, nitriles, amines, amine salts, acids, acid salts, esters of acids, hydroxyl groups, and heteroatoms selected from the group consisting of oxygen and nitrogen.

22. A method according to claim 16, wherein R is hexyl.

23. A method according to claim 16, wherein R is octyl.

24. A method of prolonging the life of a cut flower, comprising applying to the cut flower an effective life-prolonging amount of a compound of Formula I:

(I)

wherein:
n is a number from 1 to 4; and each R is independently a saturated or unsaturated, linear or branched-chain, unsubstituted or substituted, $C_6$ to $C_{20}$ alkyl, alkenyl, or alkynyl.

25. A method according to claim 24, wherein n is 1 or 2.

26. A method according to claim 24, wherein n is 1.

27. A method according to claim 24, wherein said applying step is carried out by contacting said plant to a gas of said compound.

28. A method according to claim 24, wherein said applying step is carried out by spraying said plant with a solution comprising said compound.

29. A method according to claim 24, wherein said applying step is carried out by contacting said plant to a solid comprising said compound.

30. A method according to claim 24, wherein at least one R is an alkyl, alkenyl, or alkynyl substituted with at least one substituent selected from the group consisting of halogen, amino, alkoxy, carboxy, alkoxycarbonyl, and hydroxy.

31. A method according to claim 24, wherein at least one of the carbon atoms in at least one R group is replaced by at least one constituent selected from the group consisting of ester groups, nitrites, amines, amine salts, acids, acid salts, esters of acids, hydroxyl groups, and heteroatoms selected from the group consisting of oxygen and nitrogen.

32. A method according to claim 26, wherein R is hexyl.

33. A method according to claim 26, wherein R is octyl.

34. A method of inhibiting an ethylene response in a plant, comprising applying to the plant an effective ethylene response-inhibiting amount of a composition, said composition comprising a compound of Formula I:

(I)

wherein:
n is a number from 1 to 4; and
each R is independently a saturated or unsaturated, linear or branched-chain, unsubstituted or substituted, $C_6$ to $C_{20}$ alkyl, alkenyl, or alkynyl.

35. A method according to claim 34, wherein n is 1 or 2.

36. A method according to claim 34, wherein n is 1.

37. A method according to claim 34, wherein said applying step is carried out by contacting said plant to said composition wherein said composition comprises a gas.

38. A method according to claim 34, wherein said applying step is carried out by spraying said plant with said composition and wherein said composition comprises a solution.

39. A method according to claim 34, wherein said applying step is carried out by contacting said plant to said composition and wherein said composition comprises a solid.

40. A method according to claim 34, wherein said ethylene response is fruit ripening.

41. A method according to claim 34, wherein said ethylene response is vegetable ripening.

42. A method according to claim 34, wherein said ethylene response is flower senescence.

43. A method according to claim 34, wherein said composition further comprises an inert carrier.

44. A method according to claim 34, wherein at least one R is an alkyl, alkenyl, or alkynyl substituted with at least one substituent selected from the group consisting of halogen, amino, alkoxy, carboxy, alkoxycarbonyl, and hydroxy.

45. A method according to claim 34, wherein at least one of the carbon atoms in at least one R group is replaced by at least one constituent selected from the group consisting of ester groups, nitriles, amines, amine salts, acids, acid salts, esters of acids, hydroxyl groups, and heteroatoms selected from the group consisting of oxygen and nitrogen.

46. A method according to claim 36, wherein R is hexyl.

47. A method according to claim 36, wherein R is octyl.

48. A method of inhibiting abscission in a plant, comprising applying to the plant an effective abscission-inhibiting amount of a composition, said composition comprising a compound of Formula I:

(I)

wherein:
n is a number from 1 to 4; and each R is independently a saturated or unsaturated, linear or branched-chain, unsubstituted or substituted, $C_6$ to $C_{20}$ alkyl, alkenyl, or alkynyl.

49. A method according to claim 48, wherein n is 1 or 2.

50. A method according to claim 48, wherein n is 1.

51. A method according to claim 48, wherein said applying step is carried out by contacting said plant to said composition and wherein said composition comprises a gas.

52. A method according to claim 48, wherein said applying step is carried out by spraying said plant with said composition and wherein said composition comprises a solution.

53. A method according to claim 48, wherein said applying step is carried out by contacting said plant to said composition and wherein said composition comprises a solid.

54. A method according to claim 48, wherein said composition further comprises an inert carrier.

55. A method according to claim 48, wherein at least one R is an alkyl, alkenyl, or alkynyl substituted with at least one substituent selected from the group consisting of halogen, amino, alkoxy, carboxy, alkoxycarbonyl, and hydroxy.

56. A method according to claim 48, wherein at least one of the carbon atoms in at least one R group is replaced by at least one constituent selected from the group consisting of ester groups, nitriles, amines, amine salts, acids, acid salts, esters of acids, hydroxyl groups, and heteroatoms selected from the group consisting of oxygen and nitrogen.

57. A method according to claim 50, wherein R is hexyl.

58. A method according to claim 50, wherein R is octyl.

59. A method of prolonging the life of a cut flower, comprising applying to the cut flower an effective life-prolonging amount of a composition, said composition comprising a compound of Formula I:

(I)

wherein:

n is a number from 1 to 4; and each R is independently a saturated or unsaturated, linear or branched-chain, unsubstituted or substituted, $C_6$ to $C_{20}$ alkyl, alkenyl, or alkynyl.

60. A method according to claim 59, wherein n is 1 or 2.

61. A method according to claim 59, wherein n is 1.

62. A method according to claim 59, wherein said applying step is carried out by contacting said plant to said composition and wherein said composition comprises a gas.

63. A method according to claim 59, wherein said applying step is carried out by spraying said plant with said composition and wherein said composition comprises a solution.

64. A method according to claim 59, wherein said applying step is carried out by contacting said plant to said composition and wherein said composition comprises a solid.

65. A method according to claim 59, wherein said composition further comprises an inert carrier.

66. A method according to claim 59, wherein at least one R is an alkyl, alkenyl, or alkynyl substituted with at least one substituent selected from the group consisting of halogen, amino, alkoxy, carboxy, alkoxycarbonyl, and hydroxy.

67. A method according to claim 59, wherein at least one of the carbon atoms in at least one R group is replaced by at least one constituent selected from the group consisting of ester groups, nitrites, amines, amine salts, acids, acid salts, esters of acids, hydroxyl groups, and heteroatoms selected from the group consisting of oxygen and nitrogen.

68. A method according to claim 61, wherein R is hexyl.

69. A method according to claim 61, wherein R is octyl.

* * * * *

UNITED STATES PATENT AND TRADEMARK OFFICE
CERTIFICATE OF CORRECTION

PATENT NO.    : 6,194,350 B1
DATED         : February 27, 2001
INVENTOR(S)   : Sisler It is certified that error appears in the above-identified patent and that said Letters Patent is hereby corrected as shown below:

Column 8,
Line 55, should read as follows:
-- or branched-chain, unsubstituted or substituted, $C_6$ to --.

Column 9,
Line 43, should read as follows:
-- ester groups, nitriles, amines, amine salts, acids, acid salts, --

Signed and Sealed this

Tenth Day of September, 2002

Attest:

JAMES E. ROGAN
Attesting Officer        Director of the United States Patent and Trademark Office